United States Patent
Yagci et al.

(10) Patent No.: US 9,469,309 B2
(45) Date of Patent: Oct. 18, 2016

(54) POWER SOURCE FOR AN AUTOMATION SYSTEM MECHANISM

(71) Applicant: SIEMENS HEALTHCARE DIAGNOSTICS INC., Tarrytown, NY (US)

(72) Inventors: Baris Yagci, Whippany, NJ (US); Colin Mellars, Dover, NJ (US); Benjamin Samuel Pollack, Budd Lake, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 125 days.

(21) Appl. No.: 14/376,107

(22) PCT Filed: Feb. 1, 2013

(86) PCT No.: PCT/US2013/024346
§ 371 (c)(1),
(2) Date: Jul. 31, 2014

(87) PCT Pub. No.: WO2013/116651
PCT Pub. Date: Aug. 8, 2013

(65) Prior Publication Data
US 2014/0373747 A1  Dec. 25, 2014

Related U.S. Application Data

(60) Provisional application No. 61/594,479, filed on Feb. 3, 2012.

(51) Int. Cl.
*B60L 3/00* (2006.01)
*B61B 13/00* (2006.01)
(Continued)

(52) U.S. Cl.
CPC ............. *B61B 13/00* (2013.01); *B60K 1/00* (2013.01); *B60K 1/04* (2013.01); *B60L 8/003* (2013.01);
(Continued)

(58) Field of Classification Search
CPC ..... B61B 10/00; B61B 10/001; B61B 10/02; B61B 10/022; B61B 13/00; B61B 13/08; B60L 3/00; B60L 5/00; B60L 8/00; B60L 8/003; B60L 11/00; B60L 11/02; B60L 11/04
USPC .......... 104/88.01–88.06, 281–284, 287–290, 104/292, 295
See application file for complete search history.

(56) References Cited

U.S. PATENT DOCUMENTS 4,635,560 A   1/1987  Ballantyne
6,808,021 B2 * 10/2004 Zimmerman .......... B63G 8/001
                                                114/313
(Continued)

FOREIGN PATENT DOCUMENTS

WO    2012/158520 A1   11/2012
WO    2013/177163 A1   11/2013

OTHER PUBLICATIONS

Extended EP Search Report dated Sep. 14, 2015 of corresponding European Patent Application No. 13743505.3, 3 Pages.
(Continued)

*Primary Examiner* — R. J. McCarry, Jr.

(57) ABSTRACT

Power systems for an independent carrier for transport of payloads in an automation system for in vitro diagnostic (IVD) applications. The independent carrier may include an onboard power source and an onboard electrical system electrically connected to the onboard power source for controlling movement of the carrier. The independent carrier may include an onboard propulsion system electrically connected to the onboard power source for propelling the carrier and electrically connected to the onboard electrical system for receiving a command to control the movement of the carrier. Onboard power sources may include: replaceable batteries, rechargeable batteries, induction battery charging, photovoltaic power, Peltier effect power, and external combustion engines.

20 Claims, 14 Drawing Sheets

(51) Int. Cl.
   B61C 3/02      (2006.01)
   B60L 8/00      (2006.01)
   B60L 11/18     (2006.01)
   B60K 1/00      (2006.01)
   B60K 1/04      (2006.01)
   B61C 3/00      (2006.01)
   G01N 35/04     (2006.01)

(52) U.S. Cl.
   CPC .......... B60L 11/182 (2013.01); B60L 11/1805 (2013.01); B60L 11/1816 (2013.01); B60L 11/1822 (2013.01); B60L 11/1825 (2013.01); B60L 11/1881 (2013.01); B61C 3/00 (2013.01); B61C 3/02 (2013.01); G01N 35/04 (2013.01); *B60L 2200/22* (2013.01); *B60L 2200/26* (2013.01); *B60L 2200/40* (2013.01); *G01N 2035/0489* (2013.01); *Y02T 10/7072* (2013.01); *Y02T 10/7083* (2013.01); *Y02T 30/40* (2013.01); *Y02T 90/121* (2013.01); *Y02T 90/122* (2013.01); *Y02T 90/124* (2013.01); *Y02T 90/128* (2013.01); *Y02T 90/14* (2013.01); *Y02T 90/34* (2013.01)

(56) References Cited

U.S. PATENT DOCUMENTS

| | | | |
|---|---|---|---|
| 7,591,630 B2 * | 9/2009 | Lert, Jr. | B65G 1/0492 |
| | | | 414/279 |
| 7,654,683 B2 * | 2/2010 | Ellis | H01M 10/46 |
| | | | 362/158 |
| 2005/0271555 A1 | 12/2005 | Itoh | |
| 2011/0109260 A1 * | 5/2011 | Trowbridge | H01M 4/48 |
| | | | 320/101 |

OTHER PUBLICATIONS

PCT International Search Report and Written Opinion dated Apr. 19, 2013 (15 Pages).

* cited by examiner

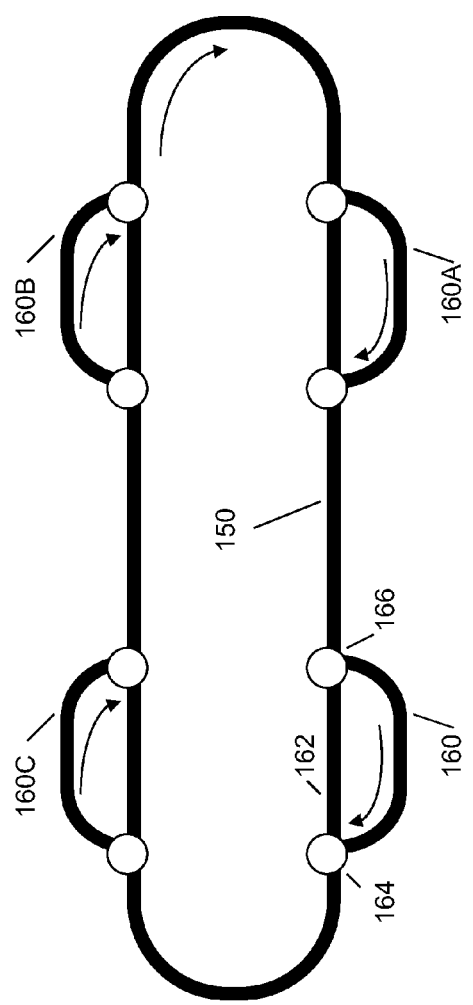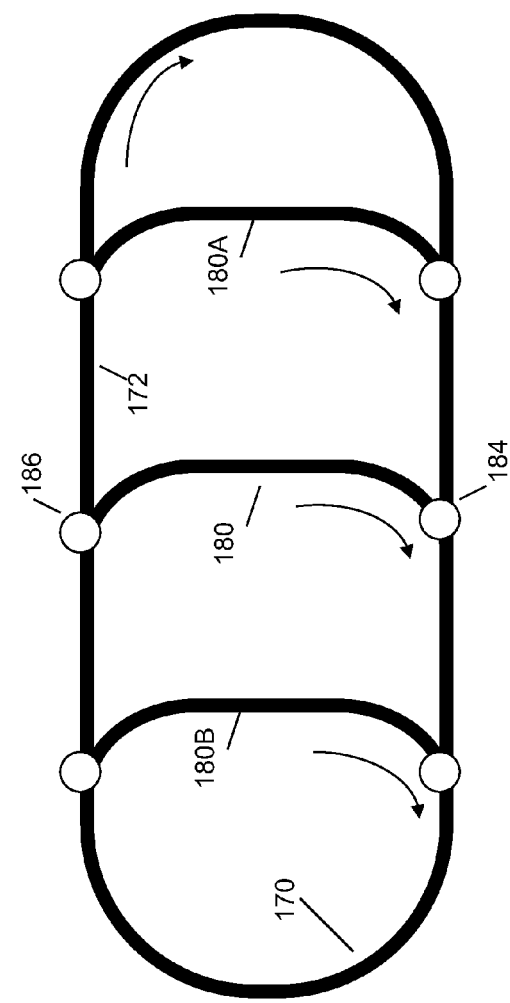

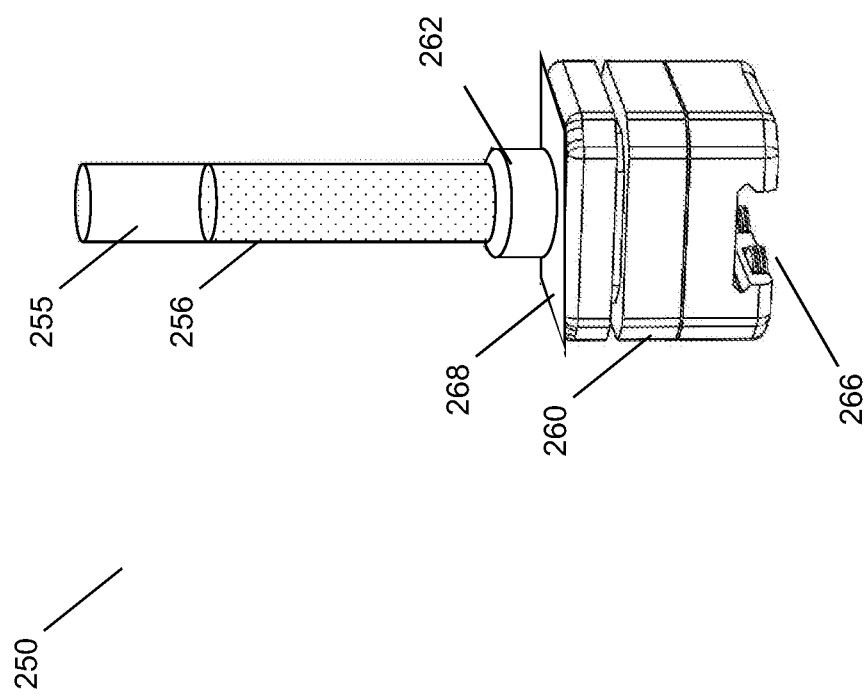

POWER SOURCE FOR AN AUTOMATION SYSTEM MECHANISM

CROSS-REFERENCE TO RELATED APPLICATIONS

This application claims priority to U.S. provisional application Ser. No. 61/594,479 filed Feb. 3, 2012, which is incorporated herein by reference in its entirety.

TECHNOLOGY FIELD

The present invention relates in general to an automation system for use in a laboratory environment and, more particularly to systems and methods for transporting patient samples for in vitro diagnostics in a clinical analyzer via active transport devices. Embodiments of the present invention are particularly well suited, but in no way limited, to power sources for independent, self-propelled carriers for moving patient samples in an in vitro diagnostics automation system.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer), which may include immunoassay (IA) and clinical chemistry (CC) stations. Some traditional IVD automation track systems comprise systems that are designed to transport samples from one fully independent module to another standalone module. This allows different types of tests to be specialized in two different stations or allows two redundant stations to be linked to increase the volume of sample throughput available. These lab automation systems, however, are often bottlenecks in multi-station analyzers. Relatively speaking, traditional lab automation systems lack large degrees of intelligence or autonomy to allow samples to independently move between stations.

In an exemplary prior art system, a friction track, much like a conveyor belt, shuttles individual carrier mechanisms, sometimes called pucks, or racks of containers between different stations. Samples may be stored in sample containers, such as test tubes that are placed into a puck by an operator or robot arm for transport between stations in an analyzer along the track. This friction track, however, can only move in one direction at a time and any samples on the track will move in the same direction at the same speed. When a sample needs to exit the friction track, gating/switching can be used to move individual pucks into offshoot paths. A drawback with this set up is that singulation must be used to control the direction of any given puck at each gate and switch. For example, if two pucks are near one another and only one puck should be redirected into an offshoot path, it becomes difficult to control a switch so that only one puck is moved into the offshoot path and ensure that the proper puck is pulled from the friction track. This has created the need in many prior art systems to have pucks stop at a gate so that individual pucks can be released and switched one at a time at each decision point on a track.

What is needed are independent carriers capable of autonomous motion for moving samples in in vitro diagnostics applications. What is also needed is a reliable power source for such independent carrier mechanisms.

SUMMARY

Embodiments of the present invention may address and overcome one or more of the above shortcomings and drawbacks by providing devices and apparatus, systems, and methods for providing a power source for powering independent, self-propelled carriers capable of autonomous motion for transporting samples in an automation system.

According to one embodiment of the present invention, an independent carrier is provided for use in autonomous transport of a payload in an in vitro diagnostic system. In one embodiment, the carrier comprises: an onboard power source; an onboard electrical system electrically connected to the onboard power source for controlling movement of the carrier; and an onboard propulsion system electrically connected to the onboard power source for propelling the carrier, and electrically connected to the onboard electrical system for receiving a command to control the movement of the carrier.

According to one embodiment of the invention, the carrier's onboard power source comprises a replaceable battery power source.

According to another embodiment of the invention, the carrier's onboard power source comprises a re-chargeable battery power source. In some embodiments, the re-chargeable battery power source may further comprise: one or more electrodes electrically connected to the rechargeable battery power source, the one or more electrodes extending from the carrier for making electrical contact with a charging element. The charging element may include one of: a charging component in a track over which the carrier travels; a charging rail along the track; or a charging station.

According to another embodiment of the invention, the carrier's onboard power source comprises an induction battery charging power source. In some embodiments, the induction battery charging power source may further comprise: a secondary induction coil onboard the carrier in close proximity to a primary induction coil external to the carrier. The secondary induction coil may pick up the induced electricity from the primary induction coil at one of: along the entire track; along select sections of track; at a charging station.

According to another embodiment of the invention, the carrier's onboard power source comprises a photovoltaic power source. In some embodiments, the photovoltaic power source may further comprise: one or more photovoltaic panels onboard the carrier positioned to face a light source to absorb photovoltaic energy radiated from the light source. The one or more photovoltaic panels may comprise a photovoltaic material that converts photovoltaic energy radiation received from the light source into electrical energy. According to one aspect of the invention, the light source is located along a side of a track over which the carrier travels. The track light source may face inward toward the center of the track, toward where the onboard photovoltaic panels are located on a side of the carrier on the side that faces the light source.

According to one aspect of some embodiments, the carrier further comprises a water-proof battery compartment.

According to another embodiment of the present invention, an analyzer for use with in vitro diagnostics includes a track configured to provide one or more paths and a plurality of carriers configured to travel along the track. The carriers include an onboard power source, an onboard electrical system electrically connected to the onboard power source for controlling movement of the one or more carriers, and an onboard propulsion system electrically connected to the onboard power source for propelling the one or more carriers and electrically connected to the onboard electrical system for receiving a command to control the movement of the one or more carriers along the track.

According to one aspect of some embodiments, the carriers include at least one track engagement mechanism configured to engage the track and move the carrier along the track and the onboard propulsion system comprises at least one actuation device configured to receive commands from the onboard electrical system to control the movement of the carrier. According to another aspect of some embodiments, the analyzer further comprise a plurality of electromagnetic coils in at least one of the track and the one or more carriers and a plurality of magnets in at least one of the other of the track and the one or more carriers. The onboard propulsion system can be configured to control the plurality of electromagnetic coils and the plurality of magnets to propel the one or more carriers along the track.

According to another aspect of some embodiments, the onboard power source can include a replaceable battery power source, a re-chargeable battery power source, an induction battery charging power source, or a photovoltaic power source.

According to another embodiment of the present invention, a method for controlling the movement of an independent carrier in an in vitro diagnostic system includes using one or more independent carriers to transport one or more payloads on a track. Each of the one or more independent carriers includes an onboard power source, an onboard electrical system electrically connected to the onboard power source, and an onboard propulsion system electrically connected to the onboard electrical system. The method further includes receiving, at the electrical system, power from the onboard power source, receiving, at the onboard propulsion system, a command from the electrical system to control the movement of the one or more carriers, and controlling the movement of the one or more carriers along the track using the onboard propulsion system.

This technology is particularly well-suited for, but by no means limited to, use with clinical analyzers for performing in vitro diagnostics (IVD).

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIGS. 2A and 2B are diagrammatic views of track geometries that can be used with the automation system embodiments disclosed herein;

FIG. 4A is a perspective view of an exemplary carrier that can be used with the embodiments disclosed herein;

DETAILED DESCRIPTION OF ILLUSTRATIVE EMBODIMENTS

Figure 1:
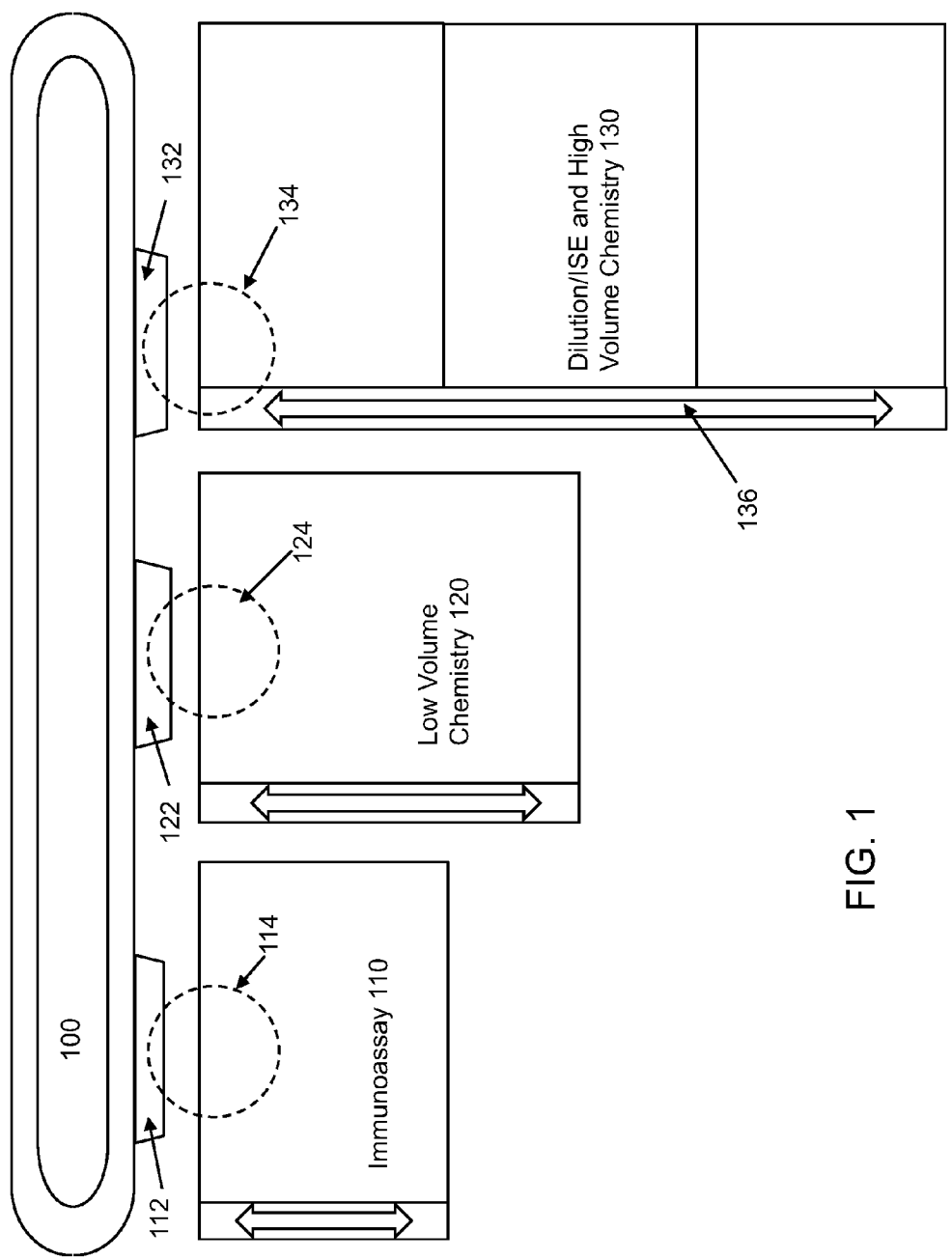
FIG. 1 is a top view of an exemplary clinical analyzer geometry that can be improved by use of the automation system embodiments disclosed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces include one or more slots (e.g., a carrier may hold one or a plurality of sample vessels).

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes; maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. WD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each mModule can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

Embodiments of the invention include improved apparatus and methods for reliably and/or automatically transporting payloads, such as patient samples and reagents to be combined with the patient samples, between stations/testing modules within an automated clinical analyzer (analyzer). Specifically, embodiments of the present invention solve the problem of passive carriers riding along a friction based track by providing self-propelled carrier for moving payloads between stations within an analyzer. Embodiments of the present invention provide power transmission and storage options for an autonomous carrier to carry in vitro diagnostics related material/samples between stations/modules. The carrier power transmission and storage options can be used as part of an automation system between process modules or inside a single module. Embodiments of the present invention may be used in lieu of, or to replace, conveyor systems, friction-based belt systems, and the like.

Sample transport systems in laboratory settings with autonomous carriers need onboard power sources to power their motion. In a modern sample automation transport system, it is desired that the carrier moves freely and is not attached to a power cord, for example. One of the possible applications of such a carrier is carrying sample tubes among in vitro diagnostics (IVD) instruments. To increase the availability of the carriers to execute their duty, charging or refueling such carriers is an important part of the overall design.

Material transport between in vitro diagnostics instruments has been done using friction based tracks that carry inactive or passive pucks. The idea of using active pucks that move on a passive track is new to the in vitro diagnostics field, hence the problem of restoring the power source onboard a carrier moving a patient fluid sample in a clinical analyzer, for example, did not exist before on these devices in the in vitro diagnostics business segment. In vitro diagnostics applications use relatively small carriers, which present unique challenges not seen in the case of large scale material handling operations, like for example Kiva Systems, where the carriers are large enough to carry batteries that can hold charge to be practical for their applications.

Providing onboard power sources for carriers in an automation system allows for more sustainable and reliable transport of payloads, such as, for example, patient fluid samples in an in vitro diagnostics (IVD) clinical analyzer. These carriers can transport samples substantially faster than prior methods, allowing reliable scheduling of tests, a reduction of traffic in the automation system, and reduced latency and reliable throughput of tests within the analyzer. Some embodiments exploit the semi-autonomy of the sample carriers to provide transit between stations in less than a single operation cycle, effectively removing or greatly reducing automation of sample placement as a performance bottleneck, and allowing more flexible sample scheduling options.

Embodiments of the present invention include systems and methods that provide a more efficient lab automation system to allow samples to be shuttled between and amongst various analyzer testing stations with less latency and more individual control. Embodiments of the present invention can reduce or eliminate queues experienced by samples traversing the automation system. Usually, samples need to undergo many different types of testing in an automated clinical analyzer (analyzer), which may not be available in a single testing station. Testing stations within an analyzer can be adapted for specialized testing. For example, immunoassays may be performed by an immunoassay station that includes certain incubation capabilities and uses specific reagents that are unique to immunoassays. Chemical analysis can be performed by a clinical analyzer and electrolyte chemistry analysis can be conducted by an ion-selective electrode (ISE) clinical analyzer. By using this modular approach, an analyzer can be adapted not only to the types of testing being done on samples, but also the frequency and volume of testing necessary to accommodate the needs of the lab. If additional immunoassay capability is needed, a lab may choose to add additional immunoassay stations and increase overall throughput for immunoassay testing in their system.

An exemplary track geometry, for use in transporting samples within an analyzer typical in prior art configurations, is shown in FIG. 1. This track can include prior art friction tracks, which may introduce problems in designing a track system. However, certain embodiments of the present invention could also use a similar geometry without necessarily employing a friction track for motion. Track 100 can be a generally oval-shaped track that conveys samples in pucks or trays between various stations, such as sample preparation or analyzing/testing stations 110, 120, and 130. Track 100 could be a single direction track or, in some instances, a linear bidirectional track. In this exemplary set-up, each analyzer 110, 120, 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to pullout 112 until analyzer 110 finishes handling a pending sample in sidecar 112 and inserts it back into the main traffic flow of track 100.

In some prior art systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station (or stations) 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system is that the separate friction tracks operate independently and control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm.

Prior art lab automation systems for analyzers generally treat individual analyzer/testing stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

FIG. 2A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload within the IVD environment, such as fluid samples, reagents, or waste. Fluids, such as patient samples, can be placed in a container or vessel, such as a test tube, vial, cuvette, etc. that can be transported by a carrier. Carriers and, by extension, payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample carrier at decision point 166 are described throughout.

FIG. 2B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path such as path 180. At decision point 186, a sample on the main track 170 can be made to continue on the main track or be diverted onto path 180. Once an analyzer station along handling path 180 is done processing the sample, the sample proceeds to decision point 184 where it may be placed back onto the main path 170.

Figure 3:
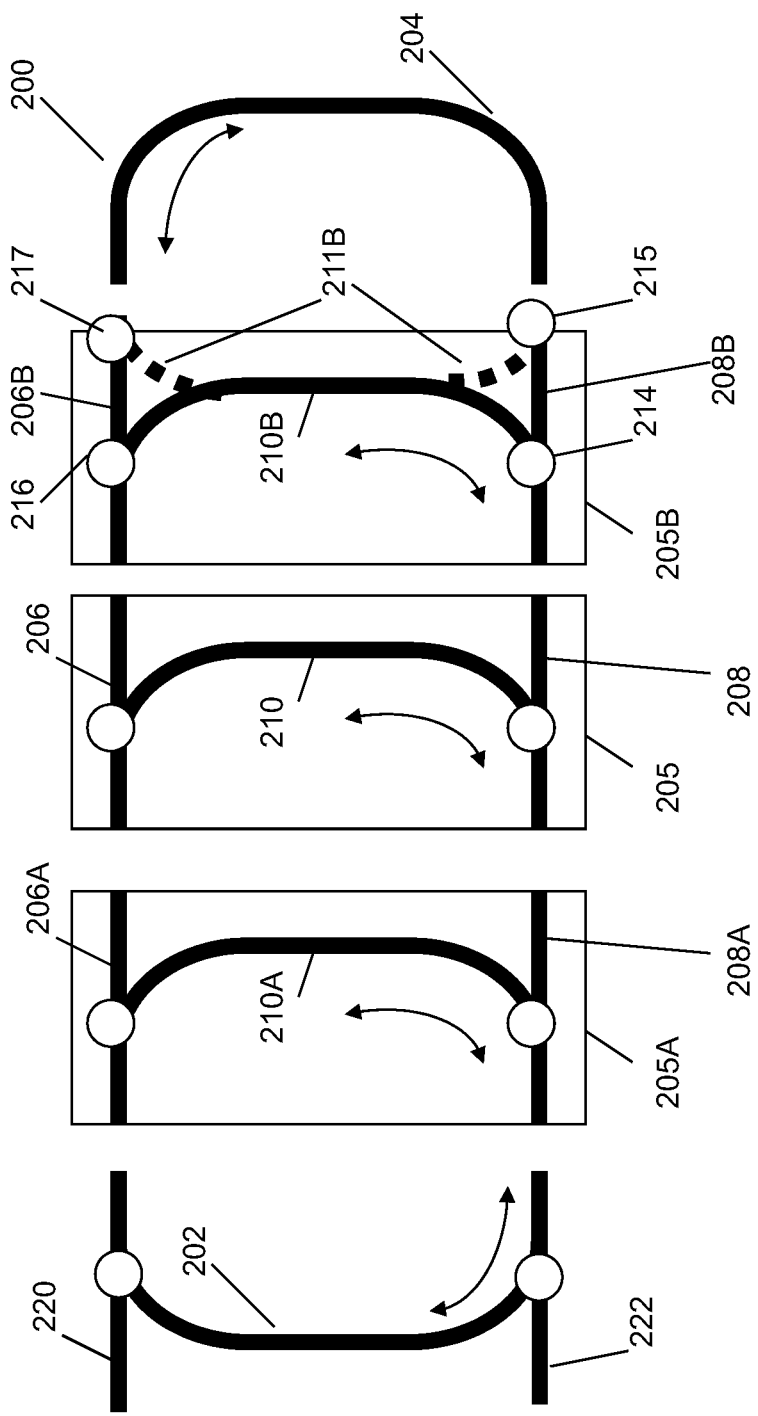
FIG. 3 is a diagrammatic view of an exemplary modular track configuration that can be used with the embodiments disclosed herein.

FIG. 3 shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems.

With respect to FIG. 3, the track 200 can be broken into modular components that are integrated into analyzer modules. In this exemplary track, modules 205, 205A, and 205B can be combined with one another and optionally other modular track components 202 and 204 to form a track similar to that shown in FIG. 2B. For instance, 205A can be a module that performs the same function as immunoassay 110 (FIG. 1), 205 can be a module that performs the same function as low-volume chemistry module 120 (FIG. 1), and 205B can be a module that performs ISE electrolyte testing, like module 130 (FIG. 1). In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, is that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other RA queues can be eliminated from the modules and the sub-paths (e.g., 210) from the automation system can be used as part of an RA or FIFO queue. That is, if the travel time for a sample between any two points can be bounded to a known time that is similar to that of a carousel (such as predictably less than a portion of an operation cycle), the track 200 can be part of the queue for a given module. For example, rather than using a carousel, module 205 can utilize samples in carriers on sub-path 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module prior knowledge of the arrival time of a sample, each module can prepare resources and interleave tests or portions of tests to more efficiently allot internal resources. In this manner, modules can operate on samples in a just-in-time manner, rather than by using large physical buffers. The effect is that the virtual queue for a given module can be much larger than the physical capacity of the sub-path serving that module, and existing scheduling algorithms can be used. Effectively, each module can treat track 200 as it would treat a sample carousel in a prior art module.

It should also be appreciated that by employing virtual queues, in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

If decision points such as 214 and 216 can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and, by extension, the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier, or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing just-in-time access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto carriers on the track 200. When the reagents on track 200 reach the appropriate module, the module can utilize mechanical systems such as an arm or a feeder system that takes the reagents off of the track and places the reagents in the reagents store for the module.

In some embodiments, the individual track portions shown in FIG. 3 and FIG. 2A and FIG. 2B can be operated independently from one another, or can be passive. Independent carrier movement provides advantages over friction-based track systems, such as non-localized conveyor belts where the entire friction track must be moved to effect movement of a sample carrier. This means that other samples also on that track must move at the same rate. This also means that if certain sections operate at different speeds, collisions between passive carriers carrying samples can occur.

FIG. 4A depicts an exemplary carrier 250 for use with the present invention. Carrier 250 can hold different payloads in different embodiments. One payload can be a sample tube 255, which contains a fluid sample 256, such as blood or urine. Other payloads may include racks of tubes or reagent cartridges. Sample carrier 250 includes a main housing 260, which can house the internal electronic components describe herein. The main housing 260 supports a bracket 262, which can accept a payload. In some embodiments, this is a shallow hole that is designed to accept a sample tube 255 and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Housing 260 is supported by guide portion 266, which allows the carrier 250 to follow a track between decision points. Guide portion 266 can include, for example, a slot to accept one or more rails in the track, providing lateral and/or vertical support. In some embodiments, the guide portion allows the carrier 250 to be guided by walls in the track, such as the walls of a trough shaped track. The guide portion 266 can also include drive mechanisms, such as friction wheels that allow a motor in the carrier housing 260 to drive the carrier or puck 250 forward or backward on the track. The guide portion 266 can include other drive components suitable for use with the embodiments described throughout, such as magnets or induction coils.

Rewritable display 268 can be provided on the top of the carrier 250. This display can include an LCD oriented panel and can be updated in real time by the carrier 250 to display status information about sample 256. By providing the electronically rewritable display on the top of the carrier 250, the status information can be viewed at a glance by an operator. This can allow an operator to quickly determine which sample he/she is looking for when there are multiple carriers 250 in a group. By placing the rewritable display on top of the carrier 250, an operator can determine status information even when multiple carriers 250 are in a drawer or rack.

Figure 4B:
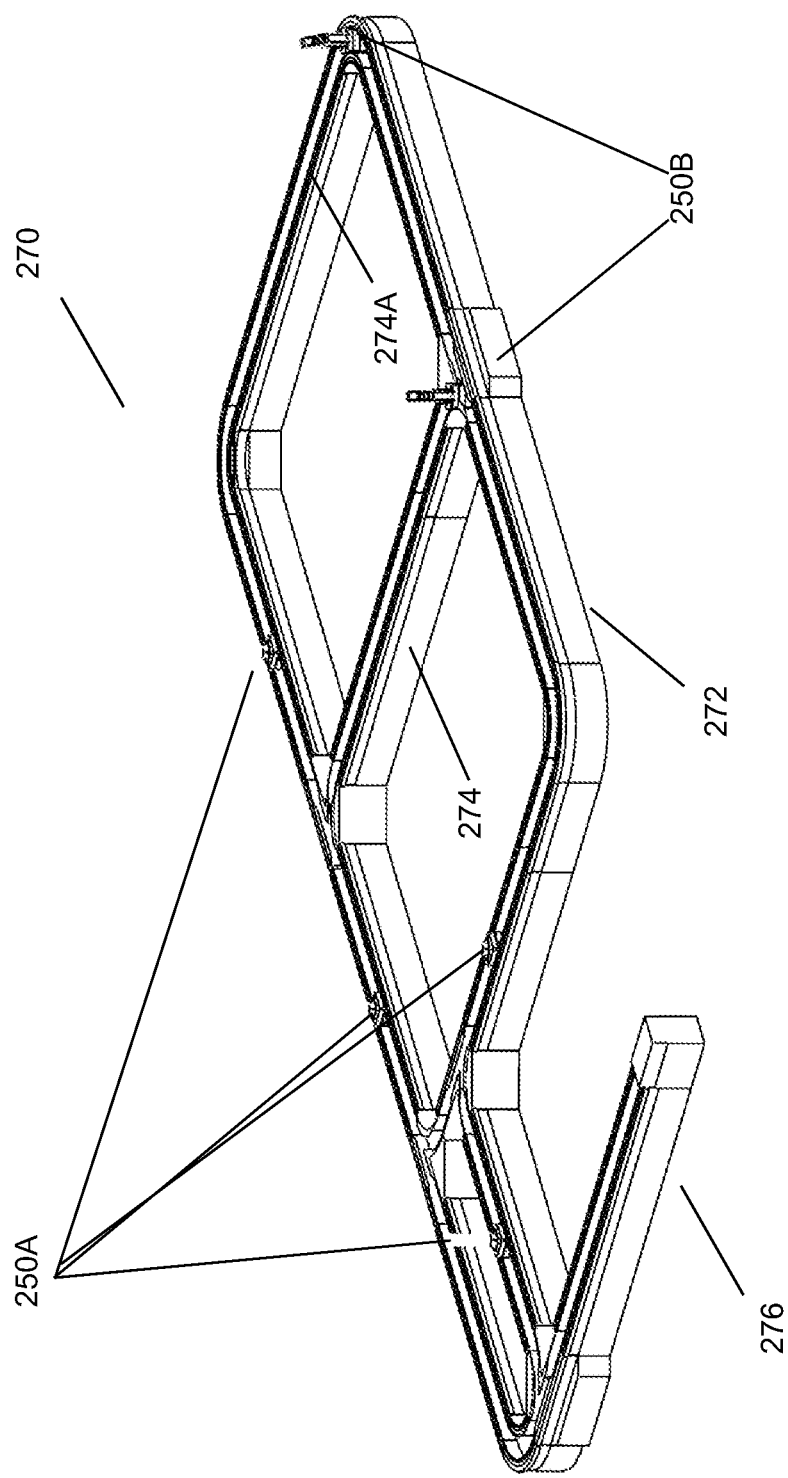
FIG. 4B is a perspective view of an exemplary track configuration that can be used with the embodiments disclosed herein.

FIG. 4B shows an exemplary track configuration 270 for use by carriers 250. In this example, carriers 250A transport sample tubes, while carriers 250B transport racks of tubes along main track 272 and/or subpaths 274 and 274A. Path 276 can be used by an operator to place samples into carriers or remove samples from these carriers.

Figure 4C:
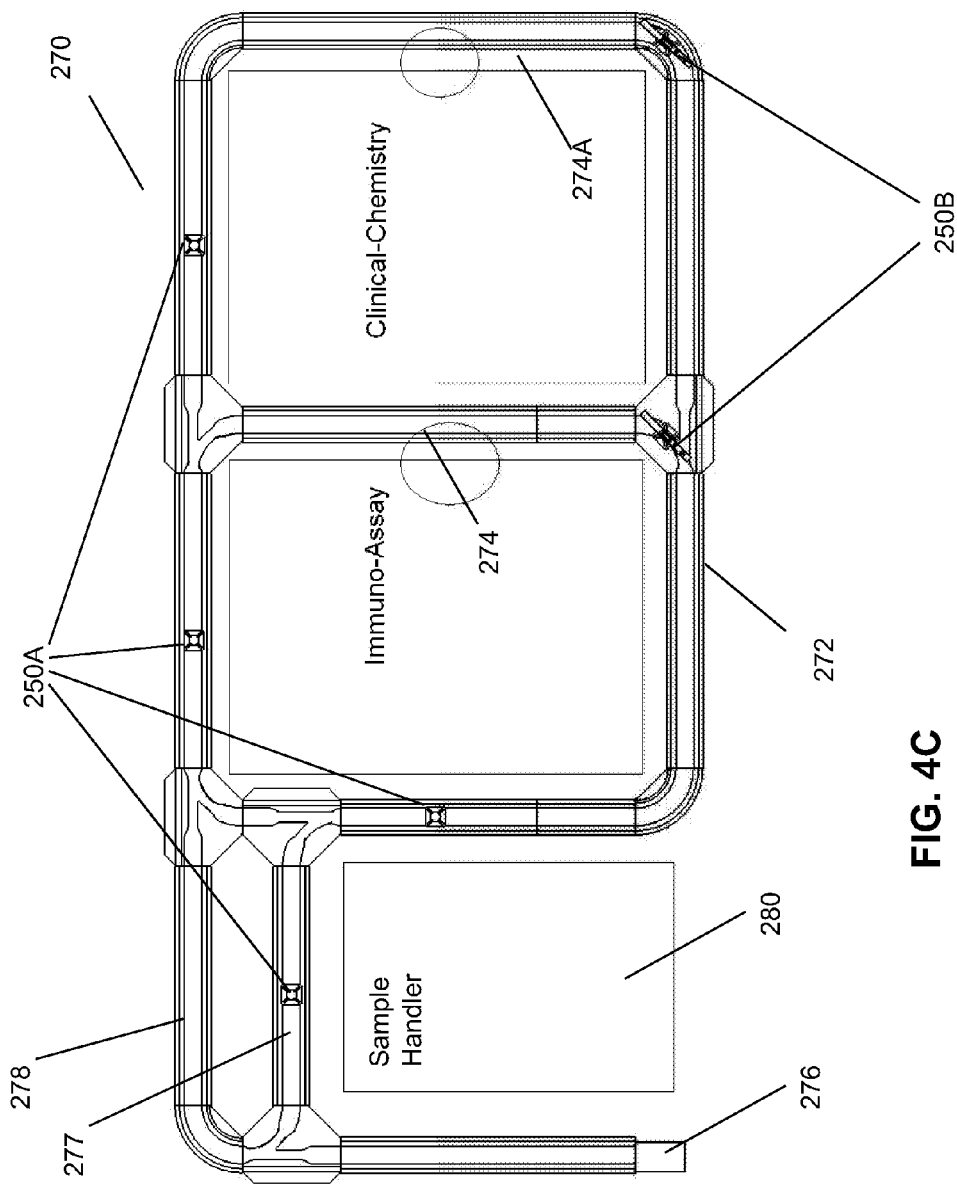
FIG. 4C is a top view of an exemplary automation system carrier that can be used with the embodiments disclosed herein.

FIG. 4C shows an additional view of an exemplary track configuration 270. In this example, sub-path 274 serves an immunoassay station, while sub-path 274A serves a clinical chemistry station. Input/output lane 276 can be served by a sample handler station 280 that uses sub-paths 277 and 278 to buffer samples for insertion or removal of the samples from the main track 272.

In some embodiments, the sample handler 280 can also load and unload samples or other payloads to/from the carriers 250A and 250B. This allows the number of carriers to be reduced to the amount needed to support payloads that are currently being used by the stations in track system 270, rather than having a vast majority of carriers sitting idle on tracks 277 and 278 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Intelligent Carriers

Whereas prior art lab automation systems utilize passive pucks or trays (e.g., the puck is a simple plastic or rubber brick that lacks active or autonomous systems, power, onboard processing, or control) to reduce cost and complexity, the inventors of the present invention have realized that the added complexity and cost necessary to integrate intelligence and autonomy into individual carriers (which can include intelligent pucks or trays in some embodiments) provides unexpected and important benefits that have been overlooked in traditional lab automation systems. Accordingly, embodiments of the present invention can utilize intelligent independent carriers to enable certain improvements over passive pucks on friction-based tracks. For example, one disadvantage of prior art track systems is that at each decision point the decision for directing a puck is made by the track by rotating the puck and reading a barcode optically. Rotating and optical reading is a relatively slow process. Furthermore, this process can be redundant because the system has knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically.

For example, a carrier can include an onboard optical reader to automatically read a barcode of a payload. The results of the scan can then be stored in the memory of a carrier if the carrier has onboard processing capability. Alternatively, an outside source, such as a hand barcode reader operated by an operator at the time of placing the sample into the carrier, can communicate the barcode information of the payload to the carrier via RF signal or other known means, such as communication protocol using temporary electrical contact or optical communication. In some embodiments, the association of the carrier with the payload can be stored external to the carrier and the identity of the carrier can be conveyed by the carrier to the system by RF, optical, or near field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

By allowing carriers to move independently, carriers can move around the track faster. One key limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For prior-art friction-based track systems, the velocity of the track is typically limited to prevent acceleration and jerk experienced by pucks from exceeding threshold amounts because the entire track moves. However, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section as appropriate, resulting in a substantially higher average speed around the track. This can assist the carrier in traversing the entire track system in less than one machine cycle of the analyzer. These machine cycles can be, for instance 20 or 40 seconds.

Similarly, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

An autonomous carrier can also include onboard processing and sensor capabilities. This can allow a carrier to determine where it is on the track and where it needs to go, rather than being directed by the track (although, in some embodiments, a central controller sends routing instructions to the carrier to be carried out). For example, position encoding or markers in the track can be read by a carrier to determine the carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position. For example, the carrier may have gyroscopes, accelerometers, or optical sensors that observe speckle patterns as the carrier moves to determine velocity or acceleration, which can be used to extrapolate a relative position.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near-field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths as appropriate. Because each carrier operates independently from one another, a carrier can do this quite quickly without necessarily stopping at each decision point and without waiting for other carriers in a queue. Because these carriers move quickly, there is less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in US Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 5:
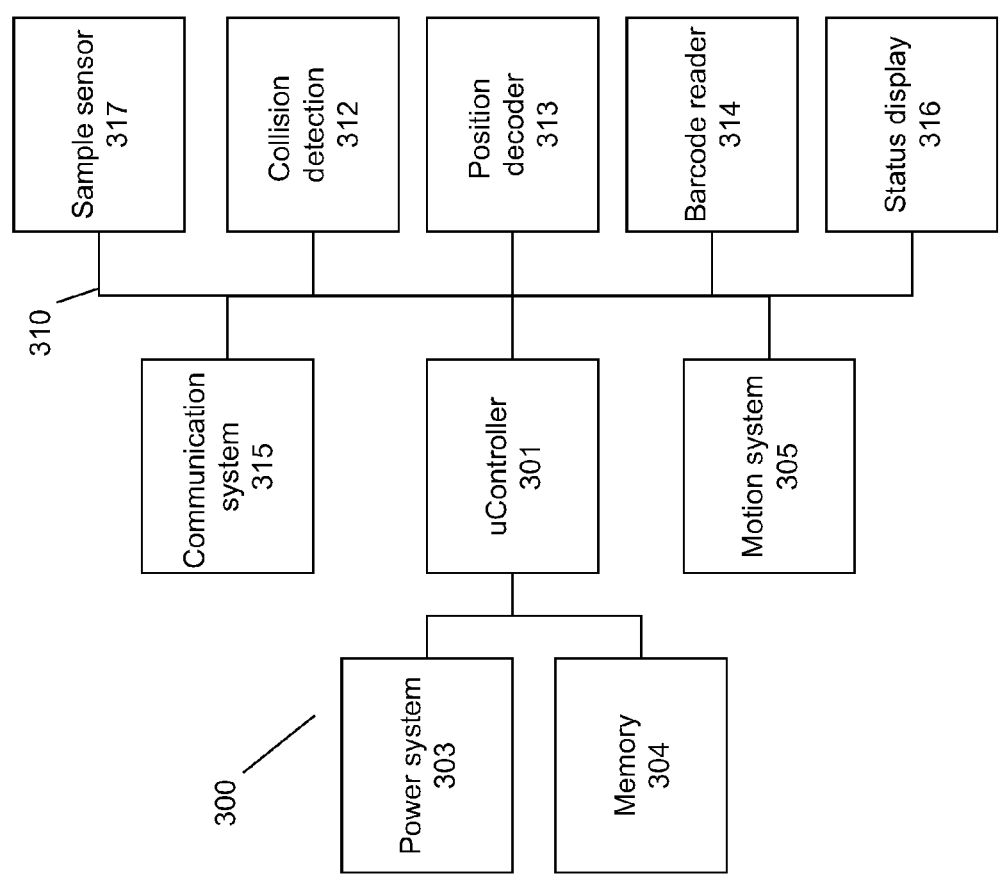
FIG. 5 is a system block diagram of the control systems including onboard active carriers that can be used with certain embodiments disclosed herein.

FIG. 5 shows a top-level system diagram of the control systems and sensors for an exemplary intelligent autonomous carrier 300. Carrier 300 is controlled by a microcontroller 301 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 303 comprises a battery that may be charged as the carrier operates, while in other embodiments, the battery is replaceable or can be manually charged when the carrier is not operating. Power system 303 can include the necessary charging electronics to maintain a battery. In other embodiments, power system 303 comprises a capacitor that may be charged by inductive or electrical contact mechanisms to obtain electrical potential from the track itself, in much the same way a subway car or model train might receive power.

Microcontroller 301 communicates with system memory 304. System memory 304 may include data and instruction memory. Instruction memory in memory 304 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 300, the carrier can keep track of its current status and uses information to intelligently route around the track or convey status information to the track or other carriers.

Microcontroller 301 is responsible for operating the motion system 305, sensors 312, 313, and 314, and communication system 315. These peripherals can be operated by the microcontroller 301 via a bus 310. Bus 310 can be any standard bus, such as a CAN bus, that is capable of communicating with the plurality of peripherals, or can include individual signal paths to individual peripherals. Peripherals can utilize their own power sources or the common power system 303.

Motion system 305 (also referred to as propulsion system) can include the control logic necessary for operating any of the motion systems described herein. For example, motion system 305 can include motor controllers in embodiments that use driven wheels. In other embodiments, motion system 305 can include the necessary logic to communicate with any active track systems necessary to provide a motive force to the carrier 300. In these embodiments, motion system 305 may be a software component executed by microcontroller 301 and utilizing communication system 315 to communicate with the track. Devices such as motors, actuators, electromagnets, and the like, that are controlled by motion system 305 can be powered by power system 303 in embodiments where these devices are onboard the carrier. External power sources can also provide power in some embodiments, such as embodiments where an LSM provides motive force by energizing coils in the track. In some embodiments, motion system 305 controls devices on or off the carrier to provide motive force. In some embodiments, the motion system 305 works with other controllers, such as controllers in the track, to coordinate motive forces, such as by requesting nearby coils in the track be energized or requesting the movement of local rollers. In these embodiments, motion system 315 can work together with communication system 315 to move the carrier.

Carrier 300 can include one or more sensors. In some embodiments, carrier 300 includes a collision detection system 312. Collision detection system 312 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 300 may be directional, having a front portion and a rear portion. By having a directional geometry, carrier 300 can include a front collision detector and a rear collision detector.

In some embodiments, collision detection information can include information received via the communication system 315. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 300 can also include a position decoder 313. This sensor can extrapolate the carrier's position as described herein. For example, position decoder 313 can include a camera or other optical means to identify landmarks in the track, or observe optical encoding in the track. In some embodiments, position decoder 313 can also include inertial sensors, magnetic sensors, or other sensors sufficient to determine a carrier's current position, direction, velocity, acceleration, and/or jerk.

Carrier 300 can optionally include a barcode reader 314. If equipped with barcode reader 314, carrier 300 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 304 via communication system 315.

Communication system 315 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 315 can include a transceiver and antenna and logic for operating an RF communication protocol. In some embodiments, communication system 315 can also include near-field communication, optical communication or electrical contact components. Information conveyed via the communications system to/from carrier 300 is described throughout this application.

In some embodiments, the carrier can also include a status display module 316. The status display module 316 can include a controller and rewritable electronic display, such as an LCD panel or E-ink display. In some embodiments, the controller is treated as an addressable portion of memory, such that the microcontroller 301 can easily update the status display 316.

In some embodiments, the carrier also includes sample sensor 317. This sensor can be used to indicate the presence or absence of a fluid container in the carrier's tube bracket (which may also be referred to as a tube holder). In some embodiments, this is a momentary mechanical switch that is depressed by the presence of a tube and not depressed when a tube is absent. This information can be used to determine the status of a tube, which can assist in the display of status information by status display module 316.

Routing

The desire for rapid transit times within an analyzer system can make routing difficult. In prior art systems, rapid routing is less critical because samples are generally stopped, singulated, and scanned at each decision point. In those systems, the routing decision for a given decision point can be made while the sample is stopped. Rapid routing decisions are generally desired, and may require determining a switching decision before a sample carrier reaches a decision point. Furthermore, because the carriers move at a rapid rate compared to the prior art, the control of the instantaneous trajectory of a sample carrier can be assisted by real-time processing in order to prevent spilling or damaging IVD samples. In some embodiments, substantially instantaneous trajectory observation and control is conducted onboard each carrier to facilitate real-time control, while the overall routing decisions are made by a central controller that manages a group of carriers. Therefore, in some embodiments of the present invention, the carriers act like semi-autonomous robots that receive global routing instructions from a central controller, but make local motion decisions substantially autonomously.

For example, when a carrier receives a sample (e.g., a patient fluid sample or other payload) a central controller managing one or more carriers determines the schedule for that carrier and instructs the carrier where to go on the track of, for example, an in vitro diagnostics automation system. This instruction can be a next-hop instruction (e.g., identifying the next leg of a route), such as going to a given decision point, moving forward to the next decision point, or turning at a given decision point. In some embodiments, the instructions can include a complete or partial list of track segments and decision points to be traversed and whether to turn at each decision point. These instructions can be communicated to the carrier from a central controller via any conventional means, including wireless or contact electrical signaling, as explained throughout this disclosure.

While following the instructions, each carrier can make a determination of the appropriate velocity, acceleration, and jerk (as used herein, acceleration includes deceleration). This can include a real-time decision of whether the carrier must slow down to avoid collision or to enter a curve without causing excessive lateral forces, or slow down before the next decision point. These decisions can be made with the assistance of any onboard sensors, as well as external information received by the carrier, such as information about the position and trajectory of nearby carriers. For example, accelerometers and/or track encoding information can be used to determine the current velocity, acceleration, and jerk, as well as the current position of a carrier. This information can be used by each carrier to determine its trajectory and/or can be conveyed to other carriers. Collision detectors, such as RF rangefinders, can determine whether or not a potential collision condition exists to assist the carrier in determining whether it needs to slow down and/or stop. This collision determination can include trajectory information about the current carrier, as well as the trajectory information about surrounding carriers received by the current carrier through observation or by receiving information from a central scheduler for the track.

Figure 6:
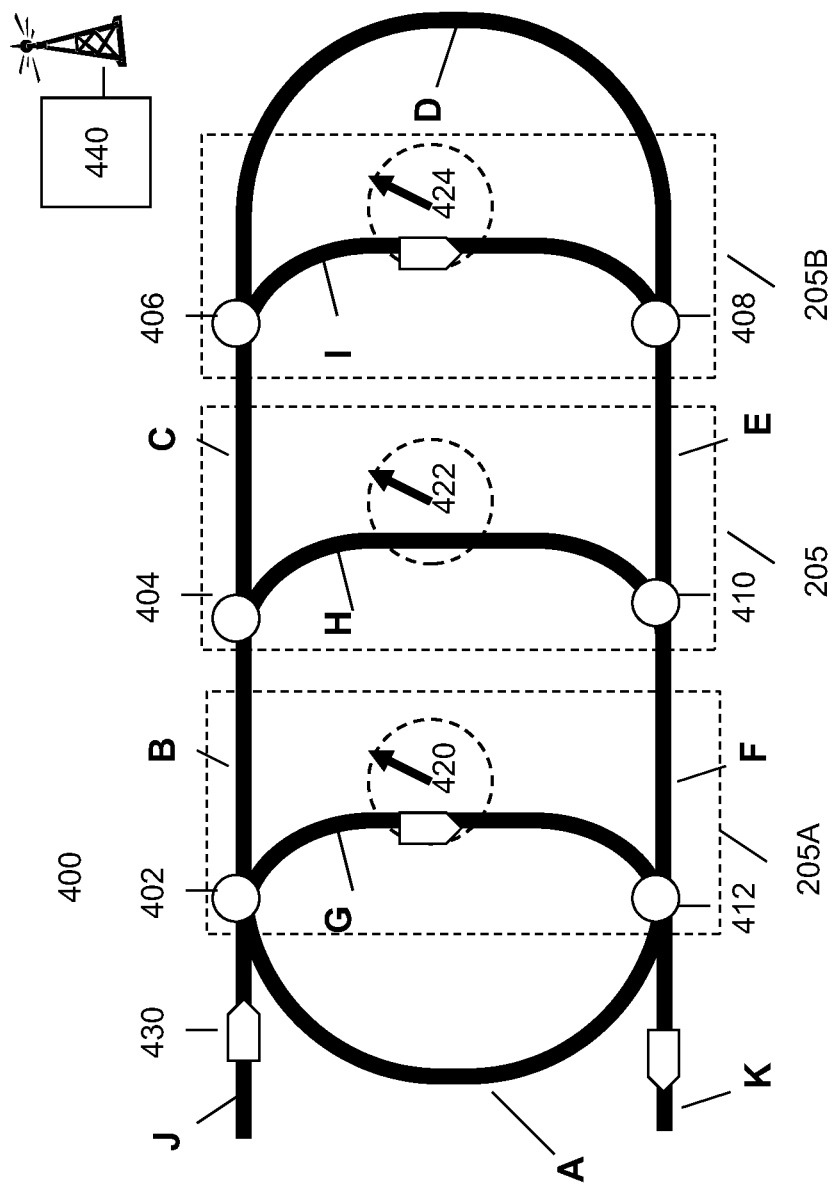
FIG. 6 is a diagrammatic view of an exemplary routes in an exemplary track configuration that can be used for navigation of carriers in certain embodiments.

FIG. 6 shows an exemplary routing scenario in automation system 400. Carrier 430 receives routing instructions from central management controller 440 via RF signaling. Carrier 430 may be any suitable embodiment of a carrier, such as carrier 300, shown in FIG. 5. Central management processor 440 can be a microprocessor, software operating on one or more processors, or other conventional computer means suitable for calculating the schedule for multiple carriers within the track system 400. Central management processor 440 can receive position information from multiple carriers, as well as any sensor information from sensors in the track system 400 and/or information reported by the carriers. Central management processor 440 uses the status information of the carriers and track as well as the identity of samples or other payload carried by the carriers and the required assays to be performed by the system on these samples.

The exemplary track system 400 shown in FIG. 6 includes a first curve segment A, that connects to straight segment B and a pullout segment G (e.g., a segment that serves a testing station), which serves analyzer/testing station 205A and pipette 420, via decision point 402. Segment B connects to straight segment C and a pullout segment H, which serves analyzer/testing station 205 and pipette 422, via decision point 404. Segment C connects to curved segment D and a pullout segment I, which serves analyzer/testing station 205B and pipette 424, via decision point 406. Segment D connects to straight segment E and the other end of pullout segment I, via decision point 408. That is, there are two direct paths between decision points 406 and 408—segments D and I (where segment I is a pullout that can be used to deliver samples to interact with pipette 424). Segment E connects to straight segment F and the other end of pullout segment H, via decision point 410. Segment F connects to curved segment A and the other end of pullout segment G, via decision point 412. In some embodiments, track system 400 includes input and output lanes J and K, which can be used to add or remove carriers at decision points 402 and 412.

In some embodiments, decision points 402-412 are passive forks in the track that carrier 430 can navigate to select a proper destination segment. In other embodiments, decision points 402-412 are active forks that can be controlled by carrier 430 or central management processor 440. In some embodiments, decision points 402-412 are electromagnetically controlled switches that respond to requests by carrier 430, such as via RF or near field communication. In some embodiments these electromagnetically controlled switches have a default position, such as straight, that the switch will return to once a carrier has been routed. By using default positions for decision points, a carrier may not need to request a position at each decision point, unless it needs to be switched at that decision point.

Scheduler central management processor 440 assigns carrier 430 a first route, Route 1, to place the carrier 430 and its payload within reach of pipette 420. Carrier 430 is instructed to travel along segment J to decision point 402 and travel onto segment G to stop at a position accessible to pipette 420. In some embodiments, carrier 430 receives the instructions and determines its current location and trajectory to determine a direction and trajectory to use to reach decision point 402. Carrier 430 can also take into account that it will be making a hard right turn at decision point 402 onto segment G. In some embodiments, decision point 402 includes a switching mechanism in the track that can operate under the control of carrier 430. In these embodiments, carrier 430 communicates with the track on approach to decision point 402 to request switching onto segment G. In other embodiments, carrier 430 may have a steering mechanism (such as moveable guide wheel, directional magnets, asymmetric brakes, or the like) that allows carrier 430 to make a right turn onto segment G at decision point 402, without the assistance of an external gate integrated into the track. In these embodiments, carrier 430 engages the steering mechanism at decision point 402 to make the turn onto segment G.

Carrier 430 can determine its rough location—its current track section, such as section J, by reading encoding in the track, such as optical encoding, or RFID tags. In some embodiments, carrier 430 uses multiple means to determine its location within the track system 400. For example, RFID tags can be used to determine generally on which track segment the carrier 430 is located, while optical encoding or other precise encoding can be used to determine the position within that track segment. This encoding can also be used to determine velocity, acceleration, or jerk by observing changes in the encoding (e.g., derivatives from the position information).

Carrier 430 can use the identification of the current track section to determine the appropriate route to the destination section either by explicit instruction received by the central management processor 440 or by looking up an appropriate route in an onboard database in memory 304, as shown in the onboard control systems in FIG. 5. In some embodiments, the carrier 430 has an understanding of how to reach section G from section J based on a map stored in the memory of carrier 430 in memory 304. This map can include a simple lookup table or a tree of track sections where each node is linked by the corresponding decision points, or vice versa. For example, upon identifying that the carrier is currently in the track section J, the onboard database can inform carrier 430 to proceed to decision point 402 to be switched to the right onto section G.

As shown in FIG. 6, carrier 430 responds to instructions for Route 1 by proceeding onto section G and stopping at a position near pipette 420. Once the carrier 430 is stopped, it can receive additional instructions from the analyzer/testing station controlling pipette 420. For example, analyzer 205A can control pipette 420 and can instruct carriers on section G to position themselves at precise points along section G. This allows analyzer/testing stations to treat track sections as random access queues. For example, once carrier 430 stops on section G, additional instructions can be conveyed via central management processor 440 or directly from analyzer 205A to the carrier 430 via RF transmission or other means, such as local optical or inductive/near-field signals. These instructions can include halting while another carrier interacts with pipette 420, and subsequently proceeding to a position accessible to pipette 420, when analyzer 205A is ready to perform one or more assays on the sample carried by carrier 430.

Once analyzer/testing station 205A has finished interacting with the sample carried by carrier 430, additional routing instructions can be sent to the carrier 430 from the central management processor 440. For example, Route 2 can include routing instructions to proceed to section H to interact with pipette 422. In some embodiments, the routing tables contained within onboard memory 304 of carrier 430 have sufficient information about the track layout to allow the carrier to route itself to section H. In other embodiments, a list of routing steps can be transmitted to carrier 430 via central management processor 440. It will be appreciated that other embodiments can include conveying any subset of the route to carrier 430 and/or sending routing instructions in a piecemeal fashion, such that carrier 430 always knows the next routing step, and optionally subsequent routing steps.

In this example, carrier 430 receives a route list representing Route 2 from central management processor 440 instructing it to proceed via section G to decision point 412. At decision point 412, carrier 430 will initiate switching onto section A by interacting with a gate or by turning as described above. Carrier 430 can take into account curved track conditions on section G and section A to ensure that acceleration and jerk conditions do not exceed a threshold requirement for the sample it carries. This can prevent spillage or instability during transit. The route information received by carrier 430 then instructs carrier 430 to proceed through decision point 402 without turning. The trajectory used in Route 2 when approaching decision point 402 can be different (e.g., faster) from that used during Route 1, because carrier 430 knows that it does not need to make a sharp right turn onto section G. In some embodiments, this allows carrier 430 to approach decision point 402 with a substantially greater velocity during Route 2 than during Route 1. By traversing decision point 402 faster if carrier 430 is not turning, carrier 430 can complete Route 2 in less time than embodiments in which carrier 430 must slow down for possible switching at each decision point. This is an improvement over the prior art, where carriers are typically halted and singulated, regardless of whether the carrier is turning or not.

After passing decision point 402, carrier 430 proceeds onto section B. At decision point 404, carrier 430 proceeds to section C. At decision point 406, carrier 430 prepares and turns onto section I, where it stops for interaction with pipette 424. Like section G, section I can act as a queue for pipette 424 and carrier 430 can be controlled under local instruction by the analyzer/testing station 205B served by section I.

When pipette 424 is done interacting with carrier 430, central management processor 440 can provide new routing instructions to carrier 430 instructing carrier 430 to proceed onto an output path K. Route 3 can be handled in the same manner as Route 1 and Route 2. Upon receiving instructions for Route 3, carrier 430 proceeds down section I to decision point 408 where it turns back onto a main track section E and proceeds past decision point 410, track section F, and decision point 412 (without needing to slow down in some embodiments), and onto section K where the carrier 430 and/or the sample can be removed from the system by an operator. Carrier 430 can then be reused for samples at input section J. Upon receiving instructions for Route 4, carrier 430 proceeds down section D to sample handling station 205C and to decision point 408, where it turns back onto a main track section E and then proceeds the same as Route 3.

Power Sources

Figure 7:
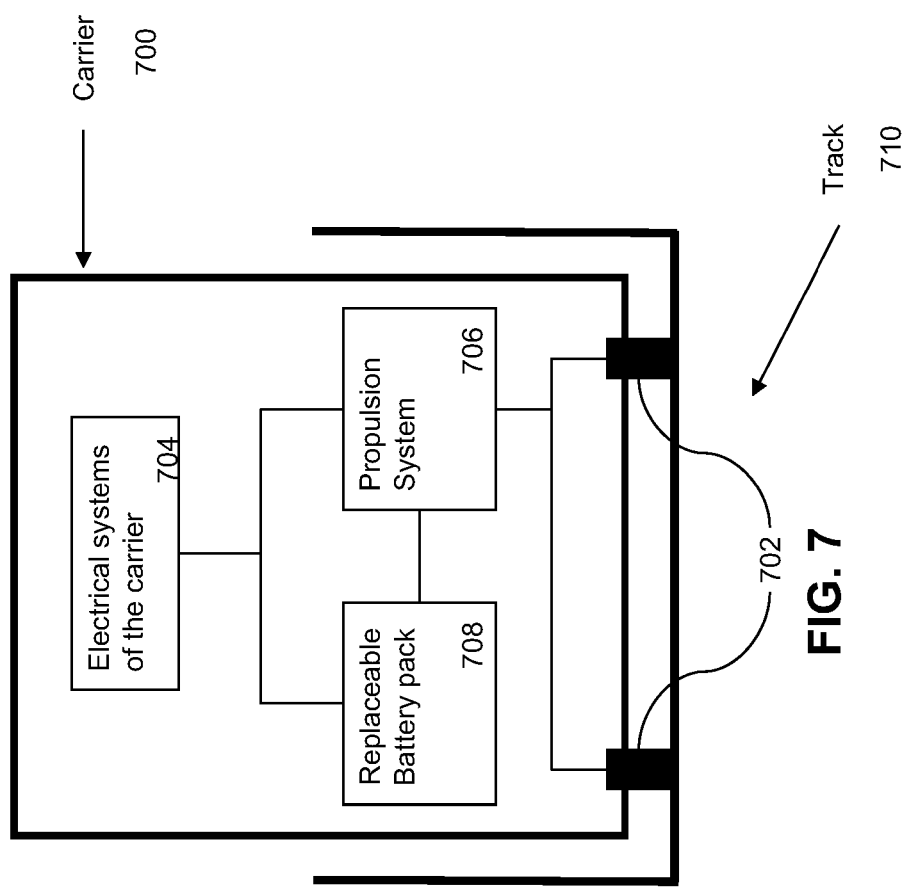
FIG. 7 shows an exemplary embodiment of a self-propelled carrier having a replaceable battery power source.

FIG. 7 shows an automation system carrier 700 having a replaceable battery power source. As shown in FIG. 7, the carrier 700 may include a track engagement mechanism 702, an onboard electrical system 704, an onboard propulsion system 706, and an onboard replaceable battery pack 708. As shown, track engagement mechanism (e.g., wheels) 702 engage and travel over a track 710. The electrical system 704 is electrically connected to the replaceable battery pack 708 to receive power for operation of one or more electrical and/or control functions of the carrier 700. A propulsion system 706 (including, e.g., a motor, output shaft, and gears) receives power from the replaceable battery pack 708 to propel the carrier 700 and receives commands from the electrical system 704 to control the movement of the carrier 700. In an embodiment having replaceable batteries, the batteries are replaced periodically by the user once the battery power is depleted or low. The carrier 700 may include an indicator (not shown) to monitor battery charge and remaining battery life, indicating to the user when a battery needs to be replaced.

Embodiments employing replaceable batteries provide an easy and convenient power source for the carrier. This also has the advantage of low cost. The carrier can also be constructed to be water-proof, or have a water-proof battery compartment so that the carrier can be washable in case of fluid spills. In an alternate embodiment, a backup battery may be stored on each carrier so that the operation of the automation system is not interrupted unpredictably. Replacing batteries is a very quick operation providing the additional advantage of a relatively low down time for the carrier while its battery is being replaced.

Figure 8:
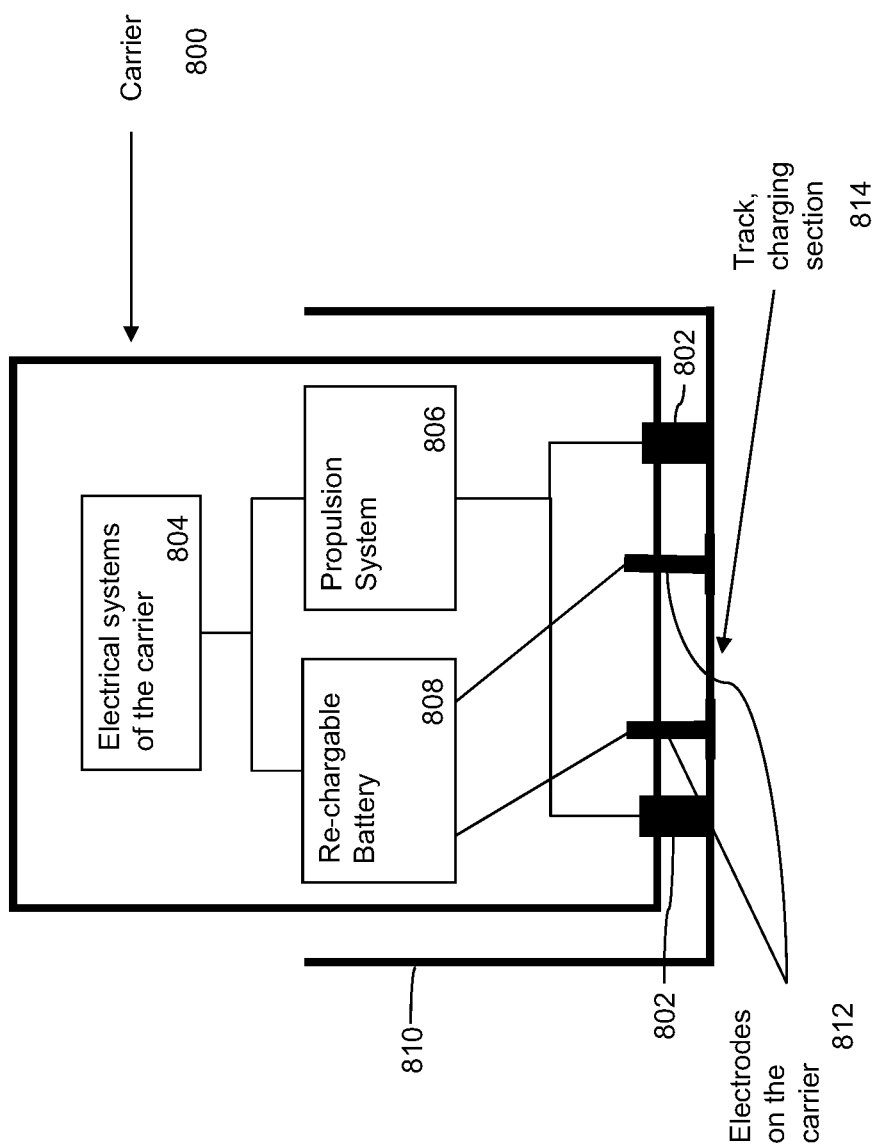
FIG. 8 shows an exemplary embodiment of a self-propelled carrier having a re-chargeable battery power source.

FIG. 8 shows an automation system carrier 800 having a rechargeable battery (or large capacitor) power source. As shown in FIG. 8, the carrier 800 may include a track engagement mechanism 802, an onboard electrical system 804, an onboard propulsion system 806, and an onboard rechargeable battery pack 808. As shown, the track engagement mechanism (e.g., wheels) 802 engages and travels over a track 810. The electrical system 804 is electrically connected to the rechargeable battery pack 808 to receive power for operation of one or more electrical and/or control functions of the carrier 800. A propulsion system 806 (e.g., a motor, output shaft, and gears) receives power from the rechargeable battery pack 808 to propel the carrier 800 and receives commands from the electrical system 804 to control the movement of the carrier 800. In the illustrated embodiment, the carrier 800 also includes electrodes 812 that extend from a bottom of the carrier 800 to engage and make electrical connection with a charging component 814. The charging component 814 may include the track 810, a charging rail, a charging station separate from, or incorporated into, the track 810, or the like. For example, charging may be provided: along the entire track; along select sections of track; at charging stations; etc. Charging may also be provided at locations along the track 810 where the carrier 800 waits or is being acted upon—e.g., at modules or queues.

An automation system having carriers with a rechargeable battery power source could have continuous charging or periodic charging. For example, the batteries may be periodically charged when the battery power is depleted or low. The carrier may include an indicator (not shown) to monitor battery charge and remaining battery life. For periodic charging, the electrical system on the carrier may determine when a charge is necessary and may instruct the carriers to go and charge themselves as the battery charge goes below a certain predetermined charge. This embodiment provides an advantage in that no user intervention is necessary. In the case of a solution that involves a charging station, the carriers may not be available to the automation system during charging. The effect of this may be mitigated by use of redundant carriers, increased battery size, and/or charge scheduling at idle times of the overall automation system, for example.

Figure 9:
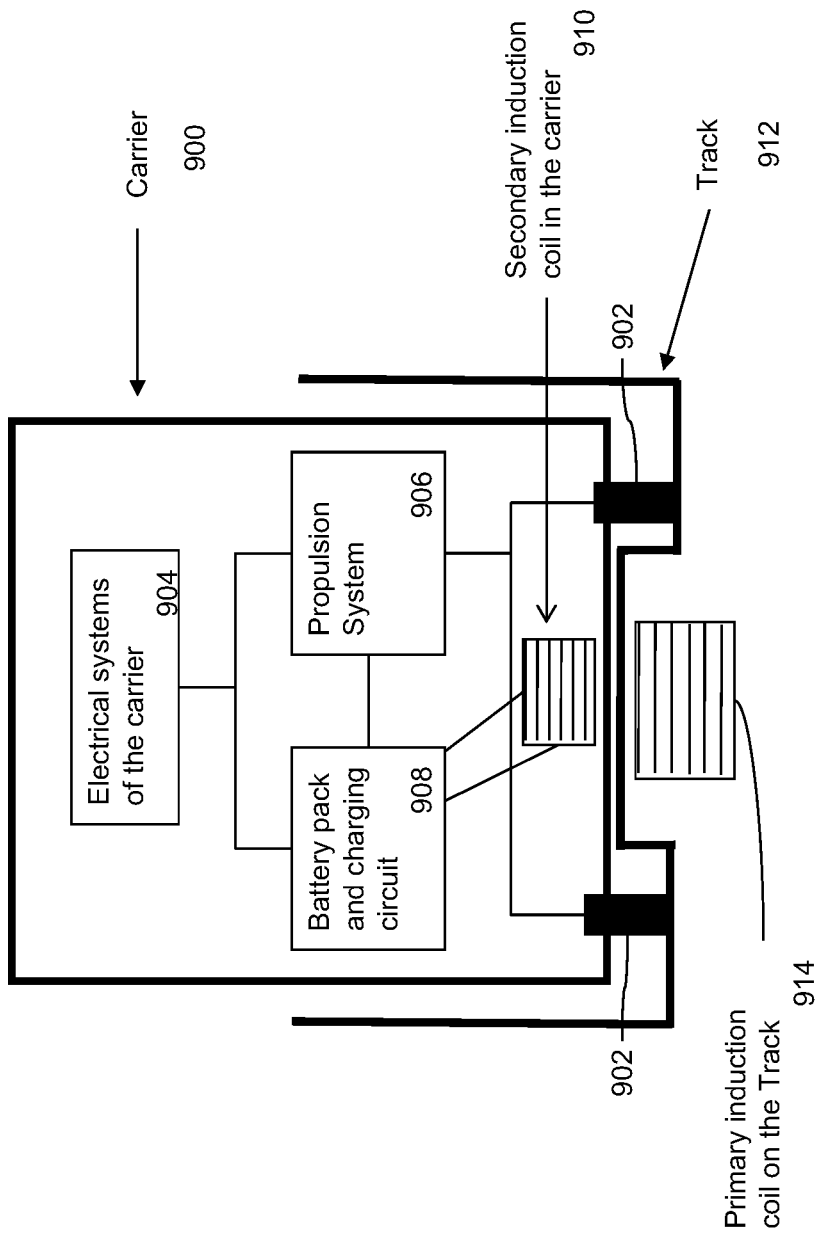
FIG. 9 shows an exemplary embodiment of a self-propelled carrier having an induction battery charging power source.

FIG. 9 shows an automation system carrier 900 having induction battery charging as its power source. As shown in FIG. 9, the carrier 900 may include a track engagement mechanism 902, an onboard electrical system 904, an onboard propulsion system 906, an onboard induction battery pack (or a capacitor) and charging circuit 908, and an onboard induction coil 910. As shown, the track engagement mechanism (e.g., wheels) 902 engages and travels over a track 912. The electrical system 904 is electrically connected to the induction battery pack 908 to receive power for operation of one or more electrical and/or control functions of the carrier 900. The propulsion system 906 (including, e.g., a motor, output shaft, and gears) receives power from the induction battery pack 908 to propel the carrier 900 and receives commands from the electrical system 904 to control the movement of the carrier 900.

In the illustrated embodiment, the track 912 and the carrier 900 include induction coils for charging the carrier's battery pack. For example, as shown in FIG. 9, the track 912 may include a primary induction coil 914 powered by external means and the carrier 900 may include a secondary induction coil 910 that picks up the induced electricity from the primary induction coil 914. As shown, the primary induction coil 914 and the secondary induction coil 910 onboard the carrier 900 are in close proximity to one another. In one embodiment, the track induction coil 914 may be located along a center portion of the track 912 and may be raised above the portion of the track 912 where the carrier wheels 902 travel. The track induction coil 914 may be provided: along the entire track; along select sections of track; at charging stations; etc. Induction charging may also be provided at locations along the track 912 where the carrier 900 waits or is being acted upon—e.g., at modules or queues.

Induction charging provides the advantage of wirelessly transferring electrical power from an external power source connected to the track induction coil to the carrier's battery pack via the carrier induction coil. Induction charging is an effective method for charging in short distances. Depending on the embodiment, the primary induction coil could be along the entire track for continuous charging, or it could be at certain charging locations along the track for periodic charging. Another advantage of induction charging is there is no danger of electric shock with this means of charging. Also, there are no exposed electrical leads or wires. Due to these advantages, the carrier can be cleaned or washed without problem. Another advantage of a charging station approach is the operating and installation costs of such a system would be much lower than a system that uses induction all around the track for charging.

Figure 10:
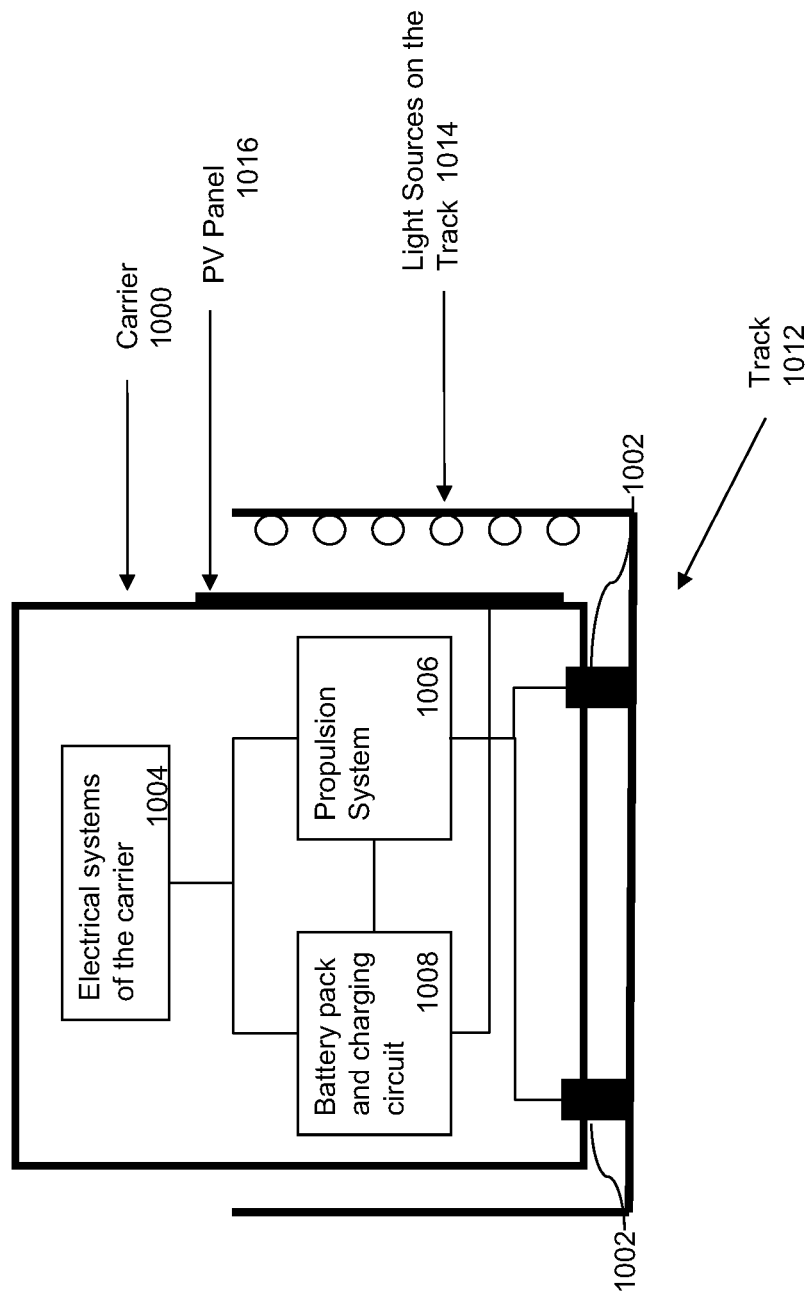
FIG. 10 shows an exemplary embodiment of a self-propelled carrier having a photovoltaic power source.

FIG. 10 shows an automation system carrier 1000 having a photovoltaic power system for battery charging. In some embodiments, the photovoltaic power system may include photovoltaics that may be employed to generate electrical power by converting light radiation into direct current electricity using semiconductors that exhibit the photovoltaic effect. The photovoltaic effect is the creation of a voltage (or a corresponding electric current) in a material upon exposure to light. In one exemplary embodiment, photovoltaic power generation may employ photovoltaic panels composed of one or more photovoltaic cells having a photovoltaic material that converts light radiation received from a light source (e.g., a light bulb, LED, etc.) into electrical energy.

As shown in FIG. 10, the carrier 1000 may include a track engagement mechanism 1002, an onboard electrical system 1004, an onboard propulsion system 1006, an onboard battery pack (or a capacitor) and charging circuit 1008, and an onboard photovoltaic module or panel 1016 comprising a plurality of photovoltaic cells. As shown, the track engagement mechanism (e.g., wheels) 1002 engages and travels over a track 1012. The electrical system 1004 is electrically connected to the battery pack and charging circuit 1008 to receive power for operation of one or more electrical and/or control functions of the carrier 1000. The propulsion system 1006 (e.g., a motor, output shaft, and gears) receives power from the battery pack 1008 to propel the carrier 1000 and receives commands from the electrical system 1004 to control the movement of the carrier 1000.

In the illustrated embodiment, the track 1012 and the carrier 1000 include photovoltaic power components for charging the carrier's onboard battery pack. For example, as shown in FIG. 10, the track 1012 may include a light source 1014 powered by external means and the carrier 1000 may include photovoltaic panel(s) 1016 that face the light source 1014 to absorb photovoltaic energy radiated from the light source 1014. As shown, the track light source 1014 may include one or more light emitting devices (e.g., any light source suitable for photovoltaic power applications), and the track light source 1014 and the carrier photovoltaic panel(s) 1016 are in close proximity to one another. In one embodiment, the track light source 1014 may be located along a side of the track 1012 and face inward toward the center of the track 1012. The photovoltaic panel(s) 1016 may be located on a side of the carrier 1000 on the side that faces the light source 1014. The track's light source 1014 may be provided: along the entire track; along select sections of track; at charging stations; etc. Photovoltaic charging may also be provided at locations along the track where the carrier waits or is being acted upon—e.g., at modules or queues.

Due to the size of carriers used in in vitro diagnostic applications, the carrier may include mini photovoltaic panels. Although ambient light of the instrument and the room in which the instrument is located may provide some light energy that the carrier photovoltaic panel may absorb, since the track may have covers on it or the ambient light sources in a lab environment can be variable, the track that hosts the carriers preferably includes lighting elements. Moreover, track lighting elements may emit light at certain light frequencies in some embodiments to maximize the power transmission, including invisible frequency range of light. In the visible range, blue light may be used for its higher energy content.

The photovoltaic panels would charge batteries (or large capacitors) onboard the carrier so that the power to carrier electrical systems, including a communication system used for navigation and identification, includes a constant source of power. This would also help the system fail gracefully if the light on the track fails for any reason. The level of power transmitted to the carriers may be adjusted through adjustment of the brightness of the light source.

A photovoltaic power system for powering the carrier provides a power transmission system that enables totally wireless power transmission and, hence, washable carriers. This solution also provides the benefit of not generating dust as a result of electrical contacts that deliver power for charging. The carrier would not necessarily be sequestered for charging and the overall utilization of the automation system would thereby increase.

Figure 11:
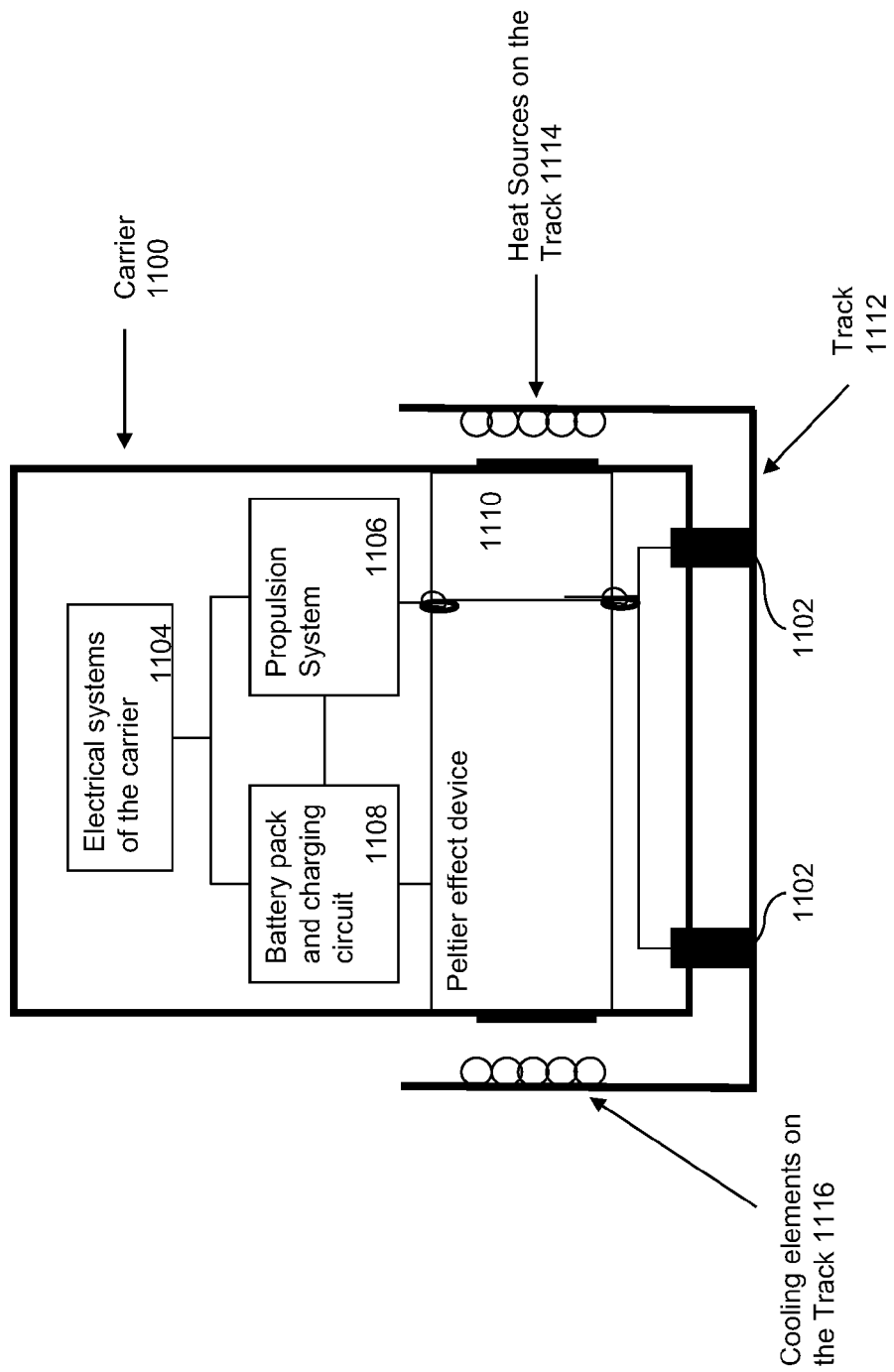
FIG. 11 shows an exemplary embodiment of a self-propelled carrier having a Peltier effect power source.

FIG. 11 shows an automation system carrier 1100 having a power system that uses Peltier effect for battery charging. As shown in FIG. 11, the carrier 1100 may include a track engagement mechanism 1102, an onboard electrical system 1104, an onboard propulsion system 1106, an onboard battery pack (or a capacitor) and charging circuit 1108, and an onboard Peltier effect device 1110. As shown, the track engagement mechanism 1102 (e.g., wheels) engages and travels over a track 1112. The electrical system 1104 is electrically connected to the battery pack and charging circuit 1108 to receive power for operation of one or more electrical and/or control functions of the carrier 1100. The propulsion system 1106 (e.g., a motor, output shaft, and gears) receives power from the battery pack 1108 to propel the carrier 1100 and receives commands from the electrical system 1104 to control the movement of the carrier 1100.

As shown in FIG. 11, the track 1112 and the carrier Peltier effect power system 1110 transfer power using thermoelectric effects for charging the onboard battery pack 1108 of an automation system carrier 1100. For example, as shown in FIG. 11, the track 1112 may include a heat source 1114 and a heat sink 1116 (e.g., cooling elements) powered by external means, and the carrier 1100 may include a Peltier effect device 1110 that interacts with the heat source 1114 and the heat sink 1116 to produce energy through the Peltier effect. As shown in the illustrated embodiment, the heat source 1114 may be located on one side of the track 1112 and the heat sink 1116 may be located on an opposite side of the track 1112 from the heat source 1114. As shown, the carrier onboard Peltier effect device 1110 is preferably located so that it is in close proximity to the track heat source 1114 and track heat sink 1116 when the carrier 1100 is traveling on the track 1112. The track's heat source and heat sink combination may be provided: along the entire track; along select sections of track; at charging stations; etc. Charging using the Peltier effect may also be provided at locations along the track where the carrier waits or is being acted upon—e.g., at modules or queues.

A Peltier device produces a voltage difference when one of its sides is heated and the other cooled. An automation system carrier provided with a Peltier device and a track that has heating on one of the walls and cooling on the other can be used to transfer power to the carrier wirelessly. The carrier could have a totally enclosed structure so that it can be cleaned easily if a fluid spill occurs. The thermoelectric device can charge an onboard battery (or a large capacitor) to ensure undisturbed power supply to the electronic components onboard the carrier.

Figure 12:
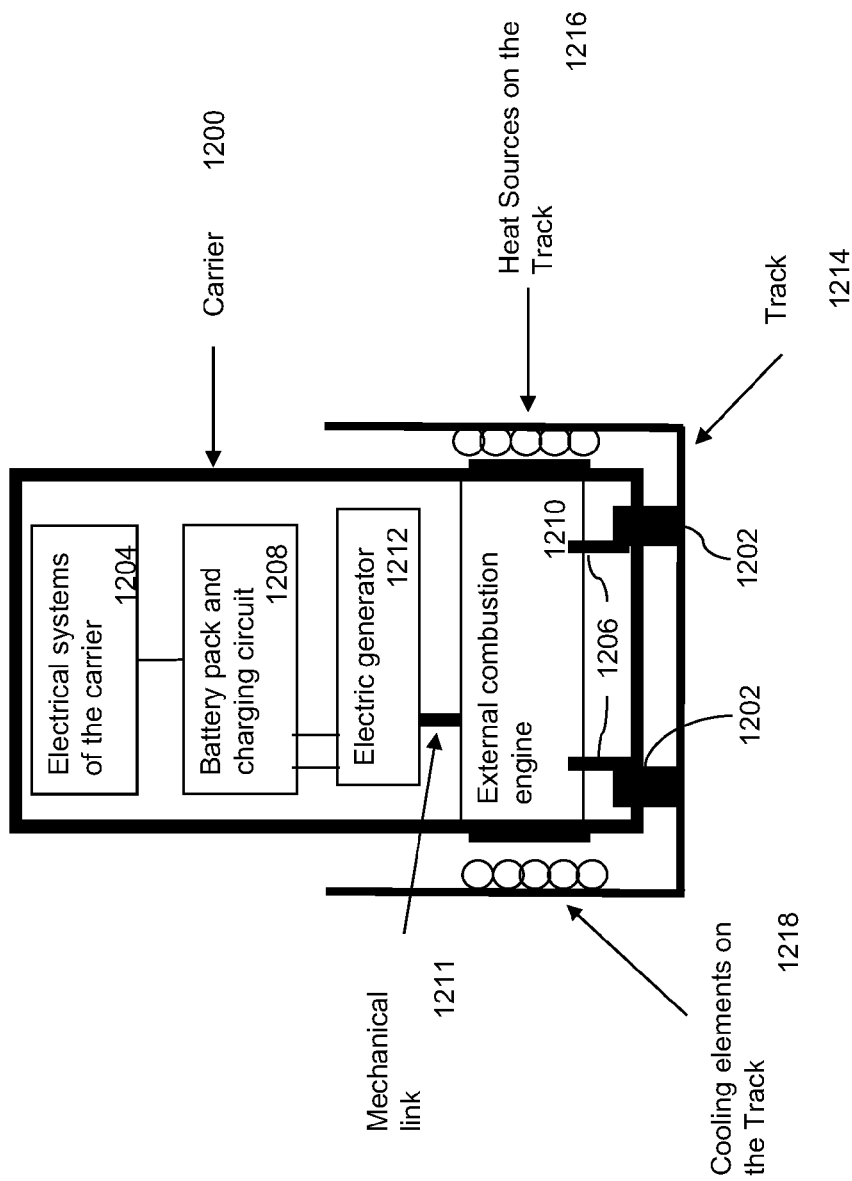
FIG. 12 shows an exemplary embodiment of a self-propelled carrier having an external combustion engine power source.

FIG. 12 shows an automation system carrier 1200 having a miniature external combustion engine. The onboard components of the carrier 1200 may be the same as the components described above with respect to FIGS. 7-11, including track engagement mechanism 1202, an onboard electrical system 1204, an onboard propulsion system 1206, and an onboard battery pack (or a capacitor) and charging circuit 1208. This embodiment, however, includes a power source comprising an external combustion engine 1210 and an electric generator 1212 connected by a mechanical link 1211. As shown, the track 1214 includes a heat source 1216 and a cooling element 1218 on the track 1214.

The miniature external combustion engine is designed to be powerful enough to move the loads (e.g., patient samples) and generate the electrical power necessary to run the electrical communication and navigation system of the independent, self-propelled, and autonomous carrier. A temperature difference is established and maintained between hot and cold sides of the external combustion engine to create power for mechanical motion of the carrier. Rankine and Stirling engines are examples of external combustion engines that can be used for this purpose. The proposed system would have a heated track wall that is in contact with, or in very close proximity to, the carrier. The heated track wall would be the hot side of the engine. The cold side of the engine can include the oppose track wall and may be either: cooled passively by heat sinks; or cooled actively by a refrigeration mechanism, for example. In this embodiment, power transmission between the track and the carrier would be through thermal means and would be wireless. If the track is heated and cooled by electric power, the overall system would not create any pollutants at the site of the carrier. Since no brush or contact is used for transferring the power, there would be minimal generation of dust and particles.

In the embodiment illustrated in FIG. 12, the engine may be used in parallel with an electric generator to charge batteries (or large capacitors) onboard the carrier 1200. An advantage of providing heating units along the track 1214 is that the carrier 1200 does not need to stop for re-charging. This would increase the availability of the carriers 1200. Alternatively, heating and cooling stations can be installed for increased electric usage efficiency, but would preferably be located in sufficient quantities and locations so as not to substantially drop the utilization of the carriers 1200.

In an alternate embodiment, miniature fossil fuel engines may be incorporated into a carrier and used as part of in vitro diagnostics automation. The miniature engine may work with fossil fuels (e.g., liquid or gas). Means for periodic refueling would be required. Also, means would be required to collect and remove any exhaust gases produced.

In yet another embodiment, fuel cells may be used produce electricity to run an electric motor on the carrier. Replacement or replenishment of the fuel for the fuel cell will be required periodically. In such an embodiment, the system should include a means of removing water vapor from the instruments. The fuel cell technology would also likely require miniaturization of components for use in IVD applications.

An instrument as used herein means a medical device or equipment used for medical purposes to diagnosis patient fluid samples. Instrument as used herein includes a clinical analyzer. Some instruments are used for veterinary labs and would also work with embodiments of the present invention. In some embodiments, patient could include most animals.

In preferred embodiments of the present invention, samples include, but are not limited to, a solution to be analyzed. A sample may include aqueous standards and verifiers, control products (e.g., protein matrix), plasma, serum, and/or urine embodiments where a carrier has some steering capability and can turn at a decision point without the assistance of the next internal switch, the carrier can engage its steering mechanism to direct it to the appropriate path upon approaching the decision point. After turning at the decision point (or proceeding without turning) a carrier returns to step 504 to determine its next trajectory.

Embodiments of the present invention may be integrated with existing analyzers and automation systems. It should be appreciated that carriers may be configured in many shapes and sizes, including layouts and physical configurations suitable for use with any contemplated analyzer or instrument. For example, in some embodiments, a carrier may include multiple slots for carrying multiple samples around an automation track. One embodiment, for example, may include a physical layout of a tube-holding portion of a carrier with multiple slots in one or more transport racks. Each rack may include multiple slots (e.g., five or more slots), each slot configured to hold a tube (e.g., a sample tube).

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. An independent carrier for use in transport of patient sample tubes in an in vitro diagnostic system, the carrier comprising:
    an onboard power source;
    a receptacle configured to receive and hold a patient sample tube;
    an onboard control system electrically connected to the onboard power source for controlling movement and for making instantaneous direction and trajectory decisions of the carrier in response to wirelessly received routing instructions; and
    an onboard propulsion system electrically connected to the onboard power source for propelling the carrier under the control of the onboard control system, in accordance with the direction and trajectory decisions.

2. The carrier of claim 1, wherein the on-board power source comprises a replaceable battery power source.

3. The carrier of claim 1, wherein the on-board power source comprises a re-chargeable battery power source.

4. The carrier of claim 3, wherein the re-chargeable battery power source further comprises: one or more electrodes electrically connected to the rechargeable battery power source, the one or more electrodes extending from the carrier for making electrical contact with a charging element comprising one of: a charging component in a track over which the carrier travels; a charging rail along the track; and a charging station.

5. The carrier of claim 1, wherein the on-board power source comprises an induction battery charging power source.

6. The carrier of claim 5, wherein the induction battery charging power source further comprises: a secondary induction coil on-board the carrier in close proximity to a primary induction coil external to the carrier, wherein the secondary induction coil picks up the induced electricity from the primary induction coil at one of: along the entire track; along select sections of track; at a charging station.

7. The carrier of claim 1, wherein the on-board power source comprises a photovoltaic power source.

8. The carrier of claim 7, wherein the photovoltaic power source further comprises: one or more photovoltaic panels on-board the carrier positioned to face a light source to absorb photovoltaic energy radiated from the light source, the one or more photovoltaic panels comprising a photovoltaic material that converts photovoltaic energy radiation received from the light source into electrical energy.

9. The carrier of claim 8, wherein the light source is located along a side of a track over which the carrier travels, the track light source faces inward toward the center of the track, and wherein the on-board photovoltaic panels are located on a side of the carrier, on the side that faces the light source.

10. The carrier of claim 1, wherein the carrier further comprises a water-proof battery compartment.

11. The carrier of claim 1, wherein the carrier is self-propelled.

12. The carrier of claim 1, wherein the propulsion system is configured to control at least one of: (ii) one or more electromagnetic coils in the carrier and (ii) one or more magnets in the carrier to control the movement of the carrier via magnetic forces.

13. An analyzer for use with in vitro diagnostics comprising:
    a track configured to provide one or more paths; and
    a plurality of carriers configured to travel along the track, including one or more carrier that comprises:
        an on-board power source;
        a receptacle configured to receive and hold a patient sample tube;
        an onboard control system electrically connected to the onboard power source for controlling movement and for making instantaneous direction and trajectory decisions of the carrier in response to wirelessly received routing instructions; and
        an onboard propulsion system electrically connected to the onboard power source for propelling the one or more carriers along the track under the control of the onboard control system, in accordance with the direction and trajectory decisions.

14. The analyzer of claim 13, wherein the one or more carrier further comprises at least one track engagement mechanism configured to engage the track and move the carrier along the track and the on-board propulsion system comprises at least one actuation device configured to receive commands from the on-board electrical system to control the movement of the carrier.

15. The analyzer of claim 13, wherein the analyzer further comprises:
    a plurality of electromagnetic coils in at least one of the track and the one or more carriers; and
    a plurality of magnets in at least one of the other of the track and the one or more carriers,
    wherein the on-board propulsion system is configured to control the plurality of electromagnetic coils and the plurality of magnets to propel the one or more carriers along the track.

16. The analyzer of claim 13, wherein the on-board power source comprises a replaceable battery power source.

17. The analyzer of claim 13, wherein the on-board power source comprises a re-chargeable battery power source.

18. The analyzer of claim 13, wherein the on-board power source comprises an induction battery charging power source.

19. The carrier of claim 13, wherein the on-board power source comprises a photovoltaic power source.

20. A method for controlling the movement of an independent carrier in an in vitro diagnostic system, the method comprising:
- using one or more independent carriers to transport one or more patient sample tubes on a track, each of the one or more independent carriers comprising:
  - an on-board power source,
  - a receptacle configured to receive and hold at least one of the patient sample tubes,
  - an on-board control system electrically connected to the on-board power source for controlling movement and for making instantaneous direction and trajectory decisions of the carrier in response to wirelessly received routing instructions, and
  - an on-board propulsion system electrically connected to the on-board electrical system for propelling the carrier under the control of the onboard control system, in accordance with the direction and trajectory decisions;
- receiving, at the control system, power from the on-board power source;
- receiving, at the on-board propulsion system, a command from the control system to control the movement of the one or more carriers; and
- controlling the movement of the one or more carriers along the track using the on-board propulsion system.

* * * * *